| | | |
|---|---|---|
| [19] | United States Patent | [11] Patent Number: 5,916,183 |
| | Reid | [45] Date of Patent: Jun. 29, 1999 |

[54] METHOD AND APPARATUS FOR TREATING EDEMA AND OTHER SWELLING DISORDERS

[76] Inventor: Tony Reid, P.O. Box 7433, Menlo Park, Calif. 94025

[21] Appl. No.: 08/860,430

[22] PCT Filed: Feb. 20, 1996

[86] PCT No.: PCT/US96/02409

§ 371 Date: Sep. 5, 1997

§ 102(e) Date: Sep. 5, 1997

[87] PCT Pub. No.: WO96/25108

PCT Pub. Date: Aug. 22, 1996

Related U.S. Application Data

[63] Continuation-in-part of application No. 08/390,866, Feb. 17, 1995, abandoned.

[51] Int. Cl.[6] ..................................................... A61H 7/00
[52] U.S. Cl. ........................... 601/134; 606/201; 606/204
[58] Field of Search .................................. 128/177, 846, 128/878; 601/134, 151, 152; 602/5, 23, 27; 606/201, 204

[56] References Cited

U.S. PATENT DOCUMENTS

| | | | |
|---|---|---|---|
| 3,888,242 | 6/1975 | Harris et al. | 601/152 |
| 4,150,442 | 4/1979 | Boone | 602/63 |
| 4,186,738 | 2/1980 | Schleicher et al. | 128/892 |
| 4,369,588 | 1/1983 | Berguer | 602/27 |

*Primary Examiner*—Richard J. Apley
*Assistant Examiner*—Benjamin K. Koo
*Attorney, Agent, or Firm*—Townsend and Townsend and Crew LLP

[57] ABSTRACT

This invention is an apparatus for treating lymphedema having a sleeve with inwardly projecting-elastomeric fingers and externally fitted pressure adjusting circular bands. When the sleeve is fitted to a patient's limb, the fingers impose a grid pattern of pressure points against skin of swollen limb. Space around and between the pressure points provide channels under the skin through which lymphatic fluids are able to migrate up the arm to the shoulder where healthy nodes process it and channel it to the large veins. Similar applications are applied to other limbs, hands, and feet with sleeves, and to the shoulder, chest wall, and back with vests.

20 Claims, 6 Drawing Sheets

METHOD AND APPARATUS FOR TREATING EDEMA AND OTHER SWELLING DISORDERS

This application is a continuation-in-part of application Ser. No. 08/390,866 filed on Feb. 17, 1995, abandoned the full disclosure of which is incorporated herein by reference.

BACKGROUND OF THE INVENTION

1. Field of the Invention

The present invention relates generally to medical devices and methods, and in particular to a device and method for removing edema fluids from a body trunk and/or extremity such as an arm or a leg.

Breast cancer is a serious disease in women, and a variety of modalities are employed in its treatment. Many of these treatments result in damage to the lymphatic and/or venous system which, in turn, can cause a condition referred to as "lymphedema." Lymphedema is the accumulation of excessive lymph fluid and swelling of subcutaneous tissues due to the obstruction or destruction of lymph vessels. In breast cancer patients, lymphedema occurs in the arm and results in painful swelling. Excessive fluid accumulation, referred to as edema, can also arise in the arms, legs and, trunk from a variety of other causes, including infection, radiation therapy, and other conditions which result in damage to or destruction of portions of the lymphatic and/or venous system.

2. Description of the Background Art

A variety of devices and methods have been proposed for the treatment of lymphedema in the arms and elsewhere. Many such devices utilize a sequential pump which works like a multiplicity of blood pressure cuffs extending from the shoulder to the hand, which contract and expand individually. When pressure is exerted by any one chamber or cuff, it applies a 'blanket pressure' (i.e. an annular pressure which completely circumscribes the limb or other body portion) to the skin directly underneath the area of that chamber. When the pressure upon that area is released, a similar blanket pressure is then applied to the portion of the arm covered by the next adjacent chamber, and so on up the arm. Such blanket pressures are applied sequentially from the distal to the proximal ends of the arm, with the intention of forcing the fluids up the arm and into the trunk of the body, where existing lymph nodes can process them.

Another prior mode of treatment has been a double walled sheath or stocking in which air pressure is introduced between the walls to squeeze the limb. It has been found that this and other similar systems, which rely on uniform blanket pressure application through the length of the afflicted limb or portions thereof, do not perform very well and in fact may interfere with the desired distal-to-proximal flow of lymphatic fluid.

We have found that when a uniform and/or excessive pressure is applied to an area for the purpose of moving fluid, the opposite effect may result. In particular, the application of pressure may: 1) compress the veins and lymph ducts, resulting in blockage; 2) augment capillary leak; and 3) prevent the lymphatic fluids from mobilizing.

Other approaches to treatment have included employment of a sheath that is separated into a number of longitudinally spaced inflatable air cells encircling the limb to be treated. These cells are successively inflated with uniform air pressure from the distal end to the proximal end of the sheath with the intent of promoting fluid flow in the desired direction. Such systems have been largely ineffectual, as they rely on air pressure being maintained at the same level or magnitude in any one of, or all, of the pressurized cells, producing a blanket effect. U.S. Pat. Nos. 2,533,504 and 2,781,041 disclose examples of such systems.

Prior U.S. Pat. No. 4,370,975 discloses an apparatus for treating lymphedema and similar fluid retention afflictions through the use of a multi-cell inflatable sheath which encompasses the swollen limb. Pressure is applied in the cells of the sheath in timed sequence from the distal cell to the proximal cell, the sequence of pressure applied also defining a decreasing gradient pressure from a maximum pressure applied in the distal cell to a minimum pressure applied in the proximal cell when all of the cells are pressurized. Generally, for each of the adjacent cells the more distal has applied a higher pressure than the more proximal. This application of gradient pressure from distal to proximal cells in time sequence comprises a cycle, and such cycle may be repeated indefinitely to promote the flow of lymphatic fluid from the afflicted limb in a proximal direction.

The problem with the above methods is that any form of blanket pressure such as that applied by pneumatic or hydraulic pressure to large afflicted areas will have at best a minimal result.

Carter, 5,063,910 shows an apparatus for treating vascular, metabolic and functional imbalance of a limb by variations in pressure of a high-density fluid, such as a mercury bath, around the limb.

The problem with this device is that the pressure applied by this means is, in fact, a blanket-pressure, which increases with the depth of the limb portion within the fluid bath, resulting in the disadvantages described above for al other pressure systems. Another disadvantage is that the patient must remain immobilized during treatment.

R. W. Lilligren et al, U.S. Pat. No. 3,454,010, shows a hollow tube-like bandage for wrapping in a spiral-like manner around the limb of a patient, into which is then applied a pneumatic pressure, which is intended to drive out excess fluids prior to surgery.

Once again the pressure applied is a uniform or blanket pressure to the skin, and so is relatively ineffective to reduce swelling.

Ewen, U.S. Pat. No. 5,257,956, shows a garment for use by post-mastectomy patients which alleviates post-operative pain and discomfort and facilitates normal activity during the recovery period. A padded vest-like garment is adapted for applying comforting pressure to the sites of removal of breast and other tissues and for holding pain relieving packages.

Again, the problem with this garment is that it applies a blanket pressure, resulting in little reduction in swelling.

Fregealle, U.S. Pat. No. 3,975,929, shows a stocking knit on a circular knitting machine which provides a gradually decreasing compressive force on the leg of the of the wearer from the ankle upwardly to the top of the stocking. Again, we believe that a uniform or blanket-pressure such as is applied by this device, is not the best method for forcing out excess lymphedema fluids.

In all of these pressure-applied methods, the patient is immobilized up to 4 hours per day, and sometimes several days in succession, suffering following treatment and soreness of the arm for many days afterwards.

It is a well established fact that special exercises following mastectomy help to mobilize lymphedema fluids; yet prior art devices contribute toward immobilizing the patient, making exercising difficult or impossible. Thus resulting in a counter-producing effect.

The cost of sequential pumps including necessary limb compression apparatus range from $500 to over $8,000. In addition, skilled technicians are necessary to operate it, thereby making treatment for lymphedema patients extremely expensive.

The following cited prior art references are relevant but distinguished from the present invention: U.S. Pat. Nos. 2,533,504, 2,699,165, 2,781,041, 2,943,859, 3,173,420, 3,454,010, 6,548,819, 3,561,435, 3,728,875, 3,845,769, 3,862,629, 3,885,554, 3,942,518, 3,975,929, 4,013,069, 4,030,488, 4,180,065, 4,320,746, 4,370,975, 4,374,518, 4,402,312, 4,552,133, 4,583,522, 4,773,397, 4,922,893, 4,938,208, 4,961,418, 5,108,426, 5,109,832, 5,117,812, 5,171,211, 5,172,689, 5,228,142, 5,233,974, 5,257,956 and 5,310,400.

SUMMARY OF THE INVENTION

The present invention provides improved apparatus and methods for treating body parts of the patient, particularly the limbs, to relieve swelling due to lymphedema and other causes. The apparatus comprise a multiplicity of pressure-applying resilient protrusions such as fingers or ridges which are arranged to apply inward pressure onto a surface of the body part to relieve swelling. The protrusions will be formed from a compressible material, such as foam rubber, and pressure will be applied by wrapping or otherwise compressing or collapsing the protrusions onto the body portion so that the fingers apply a controlled level of pressure onto a localized area over the body part surface. In all embodiments, the protrusions will be spaced-apart in an array so that the tips of the fingers or ridges which engage the body part surface apply pressure in a spaced-apart manner. Surprisingly, it has been found that applying such a distributed pattern of spaced-apart pressure points or lines against the skin effectively reduces swelling resulting from lymphedema and other edemas in a simple and cost-effective manner. In particular, the method and apparatus of the present invention do not block or inhibit fluid flow within the body part, further enhancing the body's ability to resorb the fluid responsible for swelling. An additional advantage of the device is that it is both simple and comfortable to use, enhancing patient compliance. In the treatment of lymphedema, the apparatus and method of the present invention have particularly been found to permit the release and flow back of fluid to the remaining healthy lymph nodes in a controlled manner that does not overburden such collateral lymphatic drainage.

In a specific embodiment of the present invention intended for use with the limbs of the body, i.e., the arms and legs, the resilient protrusions will have a height from a radially outward base to a radially inward tip in the range from 0.5 cm to 15 cm. The protrusions are arranged in a generally cylindrical envelope with individual fingers or ridges being aligned radially inwardly with respect to the axis of the cylindrical envelope. The length of the cylindrical envelope will depend on the body part being treated, e.g. from about 3 cm for a finger to 200 cm for trunk and legs. In an apparatus intended specifically for use with an arm, the length of the cylindrical envelope is in the range from 10 cm to 90 cm, the bases of the fingers are distributed over a generally cylindrical surface having a diameter in the range from 7.5 cm to 75 cm, and the tips of the fingers are distributed over a generally cylindrical surface having a diameter in the range from 2 cm to 15 cm. The diameters, of course, will vary widely for treatment of other body parts.

The device will further comprise at least an outer sleeve which secures the base of the fingers over the generally cylindrical outer surface. The outer sleeve will generally be formed from a non-distensible material, such as nylon fabric, permitting the fingers or ridges to be rolled to form the generally cylindrical envelope. The device will usually further comprise an axial fastener, such as a zipper, which allows the rolled fabric to be opened and closed. Alternatively or additionally, the device may comprise plurality of straps which allow the rolled fabric to be radially inwardly compressed against the body part, e.g., by cinching the straps to a desired level of internal compression. The ability to adjust the pressure applied to the body surface is important to the success of the present invention. The device may further comprise an inner sleeve to cover the radially inward tips of the fingers over a generally cylindrical surface. The inner sleeve will be intended primarily for comfort and cleanliness and will be formed from a soft, relatively thin material which allows the resilient fingers to apply pressure to the body part surface.

In a more specific embodiment the resilient protrusions will be provided by a sheet of convoluted plastic foam which, when unrolled, has a plurality of protuberances projecting upwardly from a base surface thereof. The protuberances typically form cylindrical fingers or axially aligned ridges which are tapered to a smaller width in the direction away from their base. The sheet of plastic foam can be rolled into the desired cylindrical envelope configuration described above. The tapering of the protrusions is a particular advantage since it permits rolling of the foam rubber sheet with excessive compression of the inner surface of the sheet.

A principle feature of the present invention is the provision of an improved device for applying pressure to a patient's limb for the purpose of facilitating the flow of lymphedema fluid up the limb to the shoulder. This feature includes a sleeve which can be slipped over the patient's limb and which contains a multiplicity of inwardly-pointed pressure-applying resilient fingers or ridges. The fingers are preferably arranged in rows, and the rows are arranged side-by-side such that the fingers form a grid pattern having space around each finger and between the rows. Each finger individually exerts pressure against a small area of the skin, and each small area is separated by space. The separation of individual fingers is an advantage particular in that it allows for more precise control of pressure and pressure gradient applied to the body surface.

Another feature of the present invention is that each protrusion provides controlled pressure against the adjacent body surface, which in turn allows the fluid to be mobilized back to the lymphatic and venous system. It is important that the applied pressure be sufficiently great to promote flow of excess fluid from tissue back into vascular (venous and lymphatic) circulation and thereby reduce swelling. It is equally important that the applied pressure not be so large that fluid is impeded from returning to vascular circulation. It has been found that an applied pressure in the range from 5 mmHg to 60 mmHg is usually sufficient, preferably from 10 mmHg to 45 mmHg. The precise applied pressure will usually be slightly lower than venous and lymphatic outlfow pressure, typically being about 1 mmHg to 10 mmHg below the individual patient's venous pressure.

The devices of the present invention have been found to be particularly suitable for maintaining the desired controlled pressures needed for the treatment methods. In particular, use of the foam inner layer allows the compressive force to be applied while permitting significant body movement. While other devices, such as an elastic sleeve, could initially be set at a desired pressure, body movement such as arm flexing, would result in tight constriction of the fluid circulation. Use of the resilient protuberances is particularly preferred since it allows rolling of the device over the body part without excessive compression of the inner surface of the material. Other foam and resilient materials, however, could also be used, e.g. foams which are less dense near the surface which engages the body part.

Another feature of the present invention is that each pressure finger provides graduated low pressure to the limb surface, adjustment means are also provided to increase or decrease the pressure of the fingers against the skin.

Still another feature of the present invention is the application of the apparatus to the hand in the form of a glove, or the chest or back, in the form of a vest.

Further features will become apparent in the following description of the embodiments of this invention and from the appended claims.

DESCRIPTION OF THE SPECIFIC EMBODIMENTS

Figure 1:
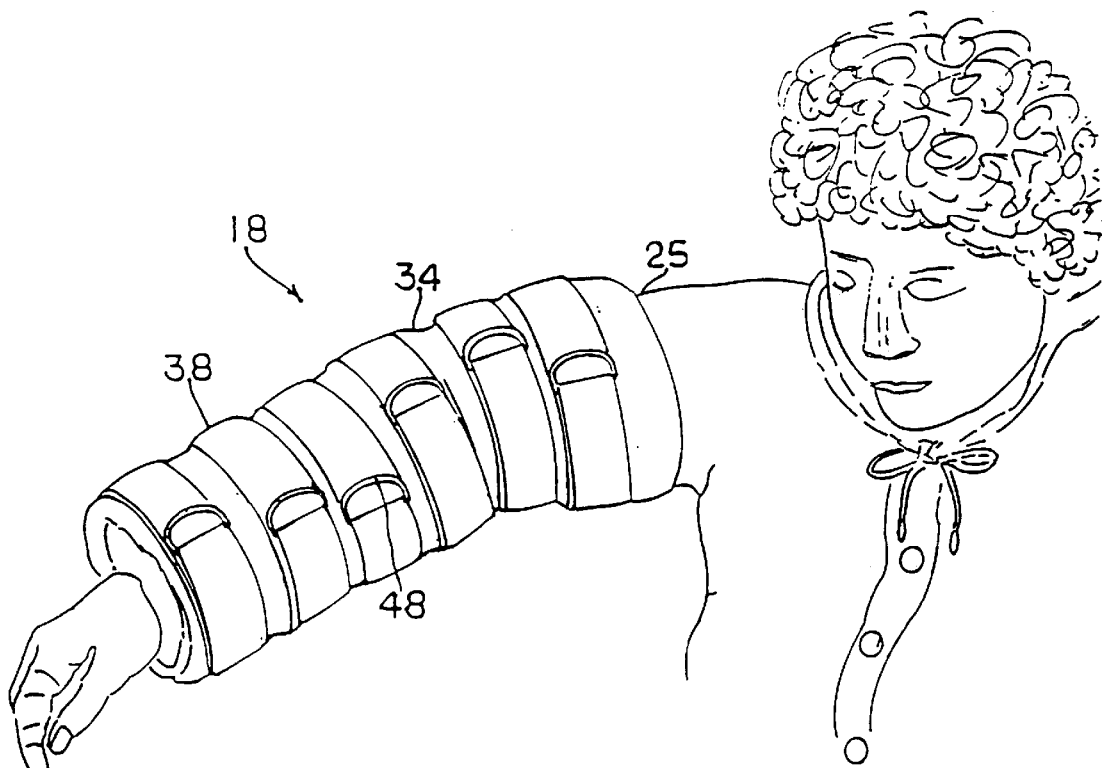
FIG. 1 is a perspective view of the sleeve of the present invention fitted to a patient.

Accordingly, FIG. 1 shows a therapeutic sleeve apparatus 18 of the present invention fitted to a patient for treating lymphedema.

Figure 2:
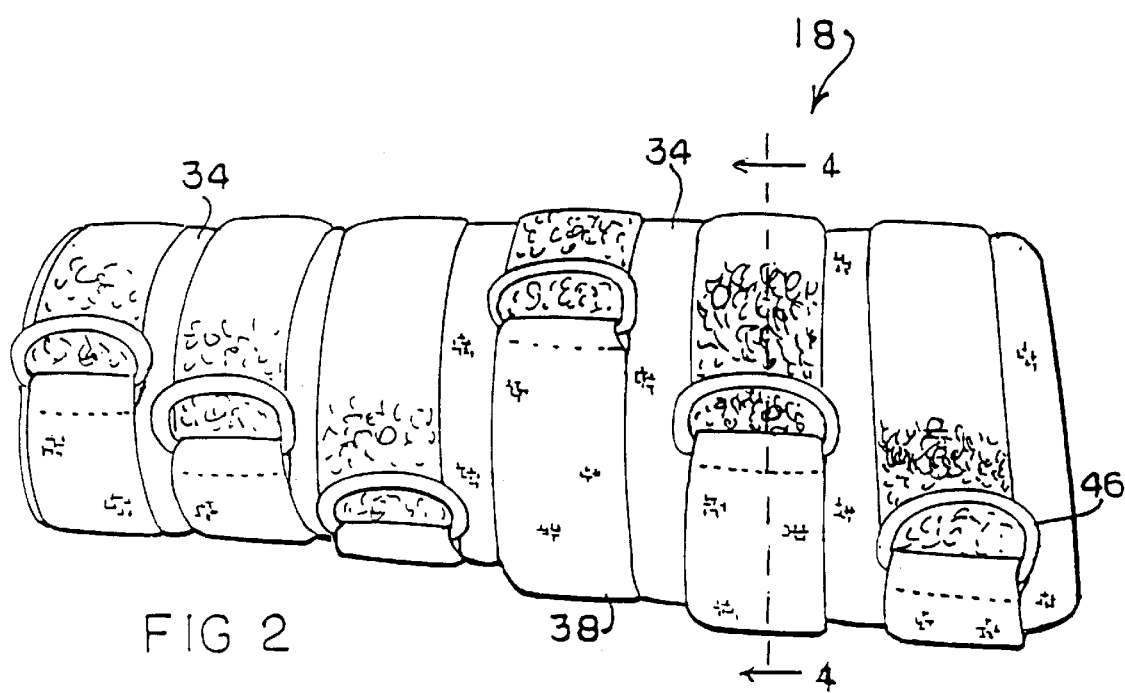
FIG. 2 is a detailed perspective view of the sleeve.
Figure 3:
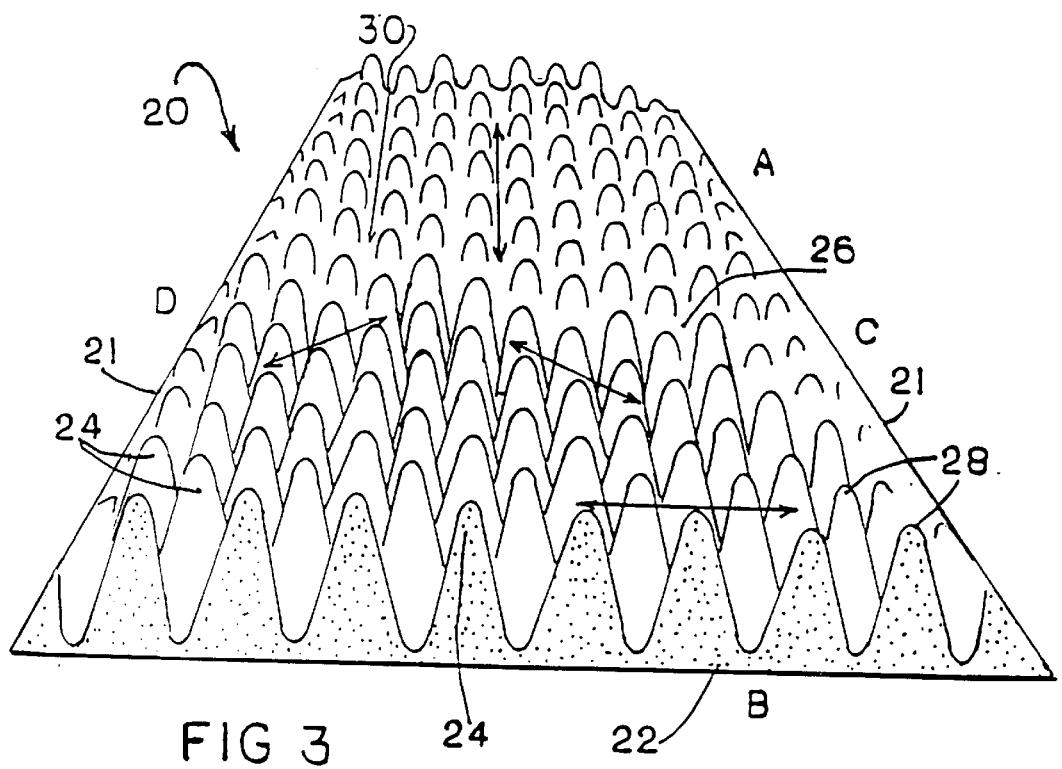
FIG. 3 is a detailed perspective view of a piece of convolute plastic foam material used in the construction of the present invention.

FIG. 2 is a detailed perspective view of sleeve 18, which is made from a quadrangle of convoluted foam material 20 (FIG. 3). Convoluted foam material is widely used as an under-sheet lining on mattresses. Tapered quadrangle 20 of convoluted foam is cut as shown in FIG. 3, the sides 21 can be angle-cut so that the edges meet flush when the foam is rolled to form a tapered sleeve. The foam comprises a base portion 22 having a multiplicity of convolutes or upward-standing fingers 24. Fingers 24 are arranged in a grid pattern formation as shown in FIG. 3, having space 26 around each finger end 28. Since the fingers are arranged in rows, avenues or channels of space 30 exist in four different directions between and through these rows as indicated by arrows A,B,C, and D, which lie longitudinally, transversely, diagonally to the right and diagonally to the left.

Figures 4, 5:
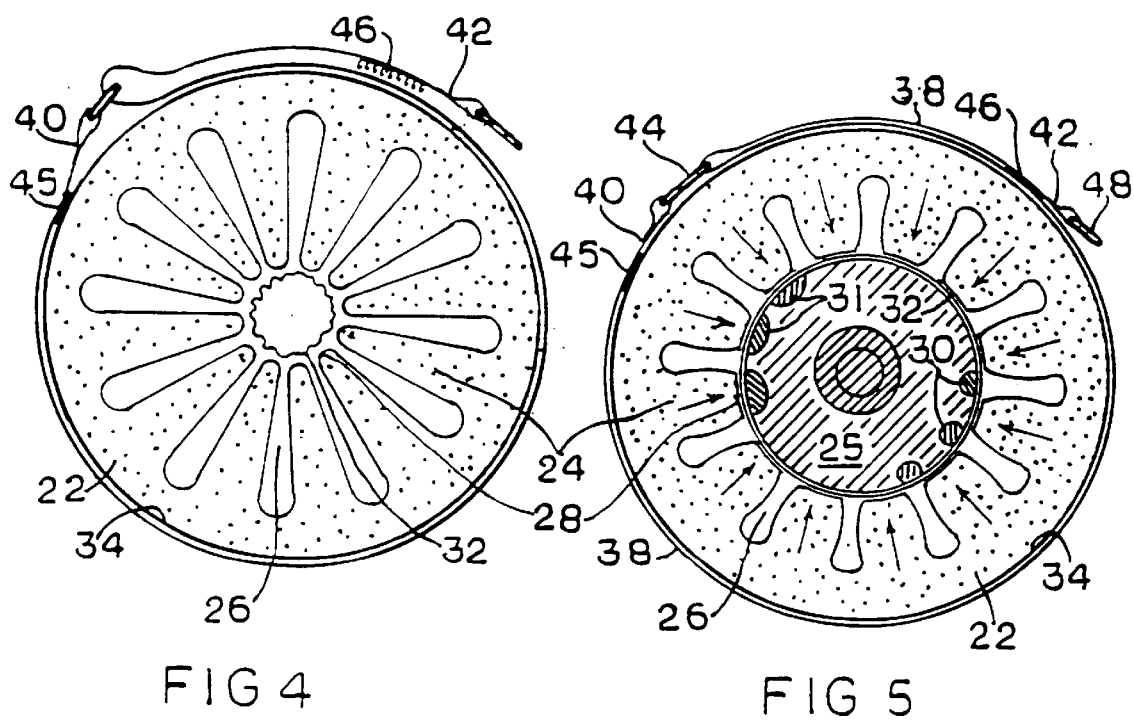
FIG. 4 is a sectional view taken along the line 4—4 of FIG. 2.
FIG. 5 is the sectional view shown in FIG. 4 when a limb is placed inside the sleeve showing compression of the pressure fingers against the limb.
Figures 6, 7:
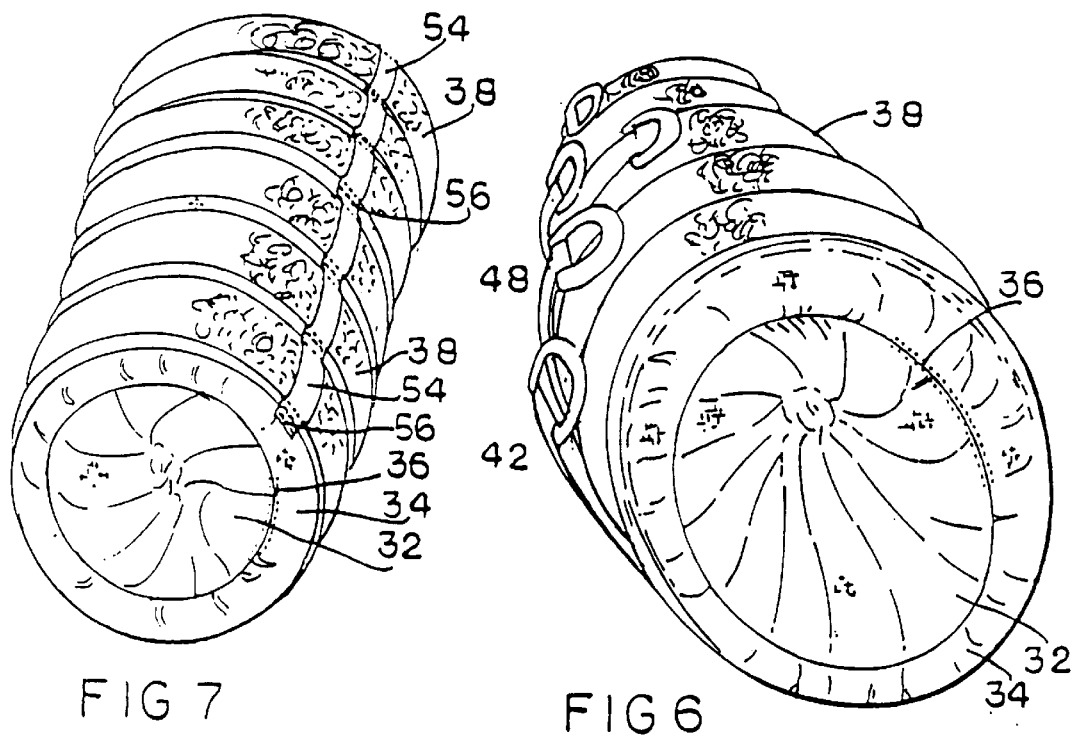
FIG. 6 is an end view of FIG. 2.
FIG. 7 is an opposite end view of FIG. 2.

Convoluted foam quadrangle 20 is rolled longitudinally, to form a slow-tapering funnel-shaped sleeve 18 (FIGS. 2, 6–9 with the fingers facing inwardly. Inwardly facing fingers 24 are best seen in cross section view FIGS. 4 and 5. Sleeve 18 is encased in fabric comprising an inner lining 32 of SPANDEX material, and an outer lining 34 of NYLON (FIGS. 2, 6–9). Any other suitable materials can also be used. Inner lining 32 and outer lining 34 are sewn together at each end, indicated by numeral 36 (FIGS. 4–6).

Figure 8:
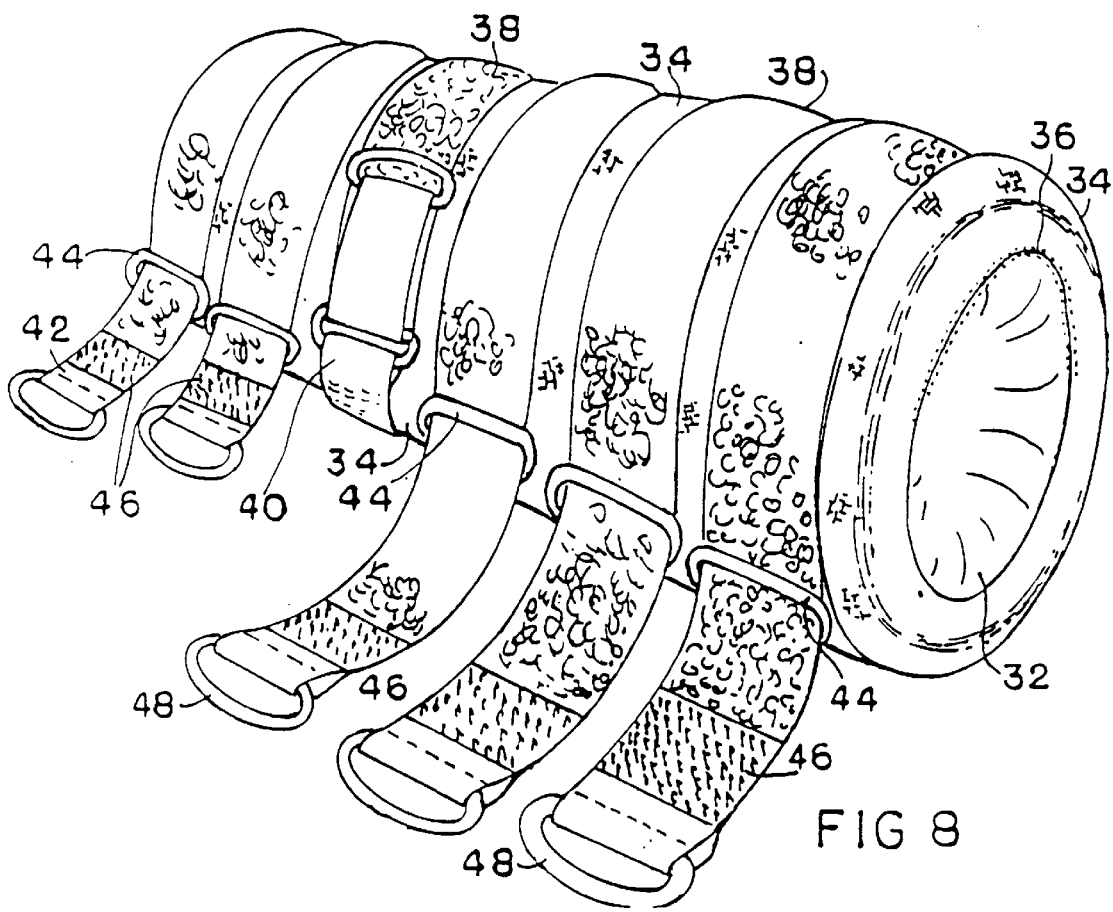
FIG. 8 Is a perspective side view of the sleeve showing VELCRO bands arrangement attached to the sleeve.
Figure 9:
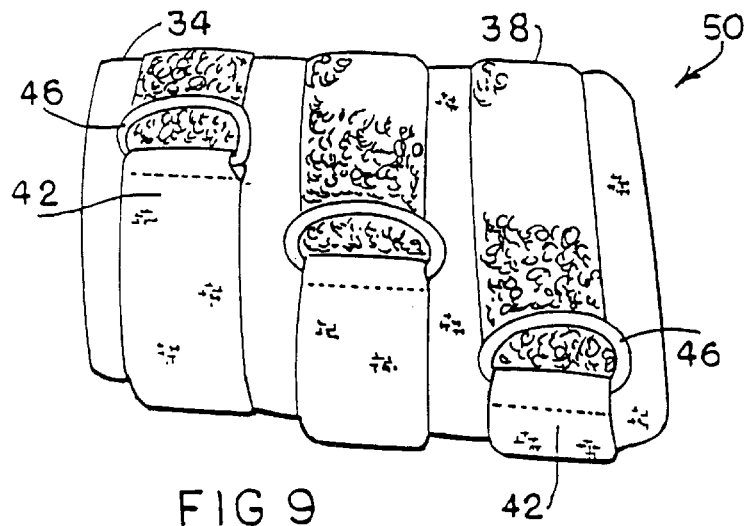
FIG. 9 is a side view of a short sleeve for enclosing a portion of a limb.

Each sleeve's outer lining 34 is encircled by a plurality of adjustable VELCRO straps or bands 38. Each band comprises a length of 50 mm (2") wide loop-side VELCRO band 38, having a first end 40 and a second end 42, (FIG. 8). First end 40 is fitted with a single loop ring 44, and is then sewn at 45 (FIGS. 4 and 5) to outer lining 34. Second end is fitted with a 50 mm×50 mm (2"×2") square 46 of hook-side VELCRO, which is sewn or adhesively attached near end 42.

Second end 42 is then passed underneath and around sleeve 18 and through single loop ring 44, then doubled back so as to attach hook-side square 46 to loop-side band 38. A "D" ring 48, or a self-separating pad, (not shown) is attached to end 42).

Each webbing strap or band 38 can be adjusted tighter or looser to increase or decrease inward pressure of fingers 24 against the patient's limb. The adjustment can then be secured by attaching hook-side square 46 at end 42 to loop-side band 38.

In like manner, an additional number of encircling webbing bands 38 are progressively attached along the remainder of the sleeve's outer lining 34, keeping them 12.5 mm (½") apart (FIGS. 2 and 8).

A short sleeve 50 (FIG. 9), which is about 225 mm (9") long, will require three 50 mm (2") wide bands. A 400 mm (16") long sleeve 18, FIG. 2, will require 6 bands, while a 76 cm to 99 cm (30" to 39") long sleeve 52, (FIG. 10), for a lower limb, would require about 12 to 16 bands.

In addition, to sewing end 40 to the sleeve's outer lining 34 along one side of sleeve 18, a series of loops 54 (FIG. 7) are sewn at 56 to the opposite side of the sleeve, so as to slidably locate bands 38 in a regular spaced-apart relationship along the sleeve. Each band 38 is free to slip endwise through loops 54 during tightening or loosening of the bands.

Convoluted foam material can be made in a variety of material density, resulting in harder or softer pressure fingers. Soft for patients requiring a lower level of applied pressure while more dense fingers are used for patients requiring high levels of applied pressure, as described more fully below.

Figure 10:
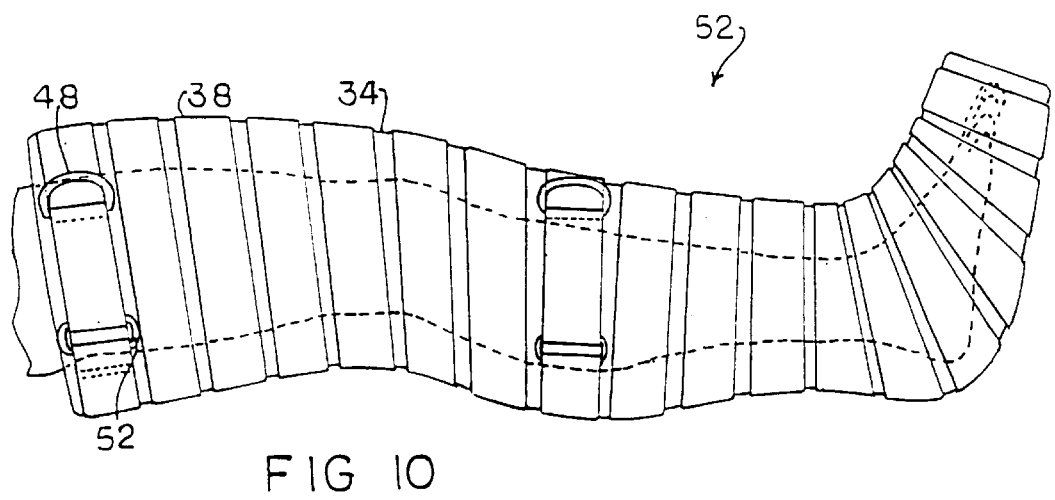
FIG. 10 is a side view of a sleeve for enclosing a lower limb including the foot.

FIG. 10 shows a sleeve 52 for a lower limb, which also includes patient's foot. These can be made in various lengths to accommodate longer and shorter limbs.

When a plane of convoluted foam material shown in FIG. 2, is rolled into a sleeve with the fingers facing inwardly, the fingers and the finger ends 28 are then located closer together as seen in FIGS. 4 and 5. However, the fingers still maintain the original grid formation, and also a space between the fingers, and between the rows of fingers still exist in the four directions mentioned above.

When a limb, such as arm 25 (FIGS. 1 and 5) is placed inside the sleeve, and tightening adjustments made with VELCRO bands 38, the elastomeric pressure fingers 24 press against skin 29 around and along the full length of the arm. Each pressure finger is separated from the adjacent pressure finger by channel 30 against which no pressure is applied. Shaded areas 31 (FIG. 5) indicate the areas not under pressure, which form the channels for conveying lymphedema fluids.

It is believed that each small area under pressure changes the interstitial pressure in the tissues, moving lymphatic fluids into and along these channels to the lymphatic and venous drainage system.

Figure 11:
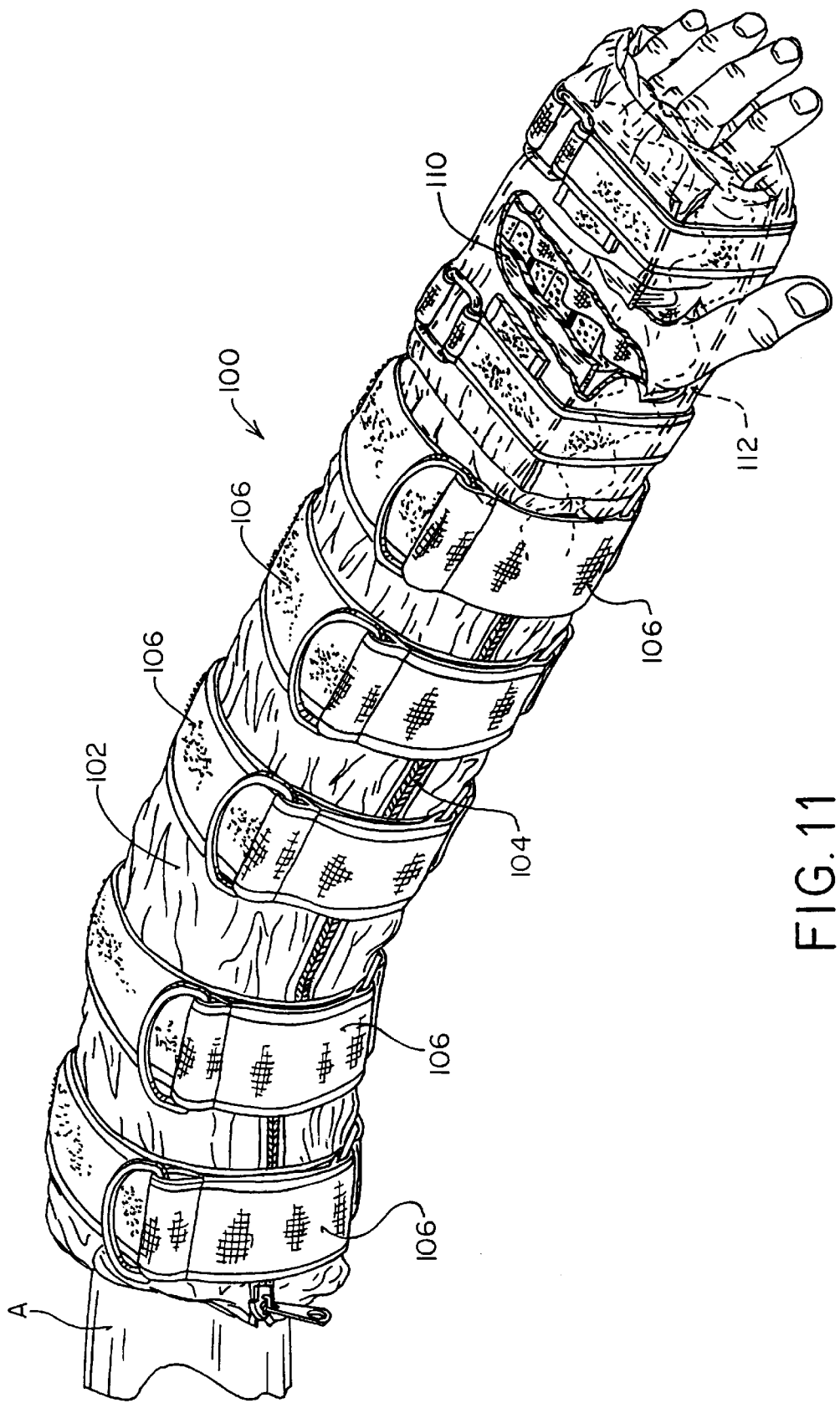
FIG. 11 is a perspective view of a second embodiment of a sleeve constructed in accordance with the principles of the present invention fitted to an arm of a patient.
Figure 12:
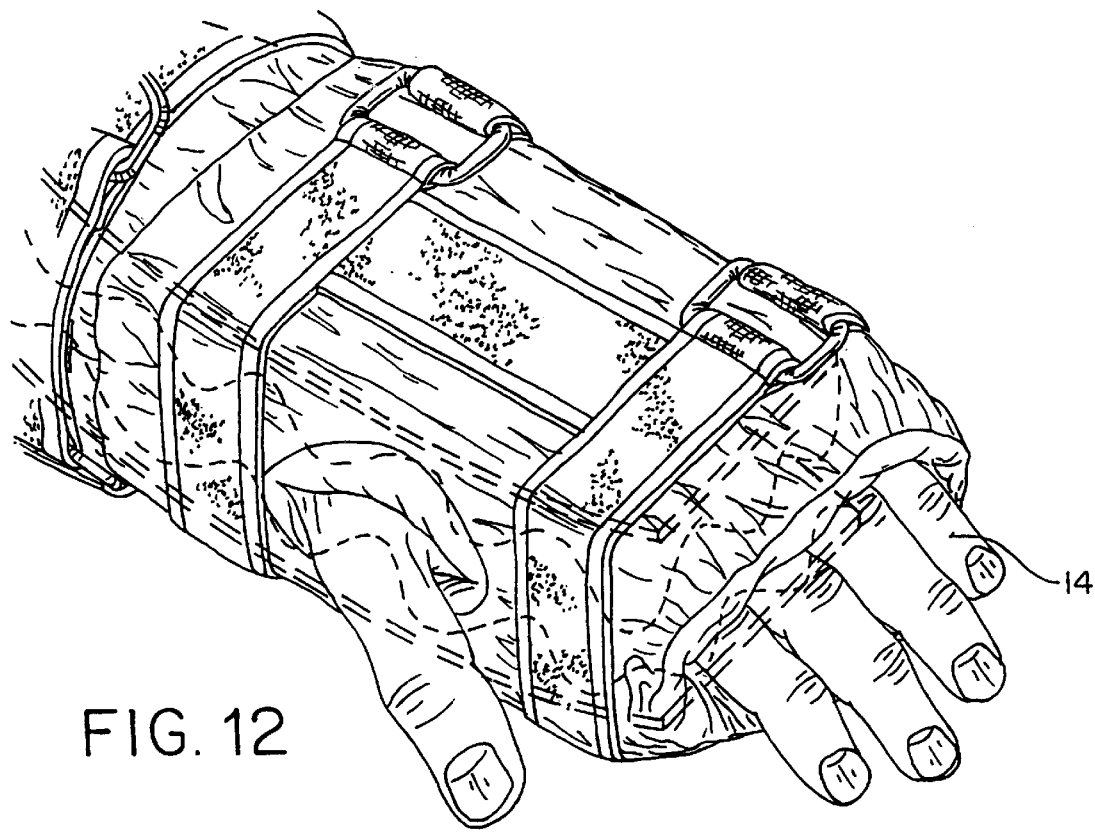
FIG. 12 is a detailed view of the distal end of the sleeve of FIG. 11.
Figure 13:
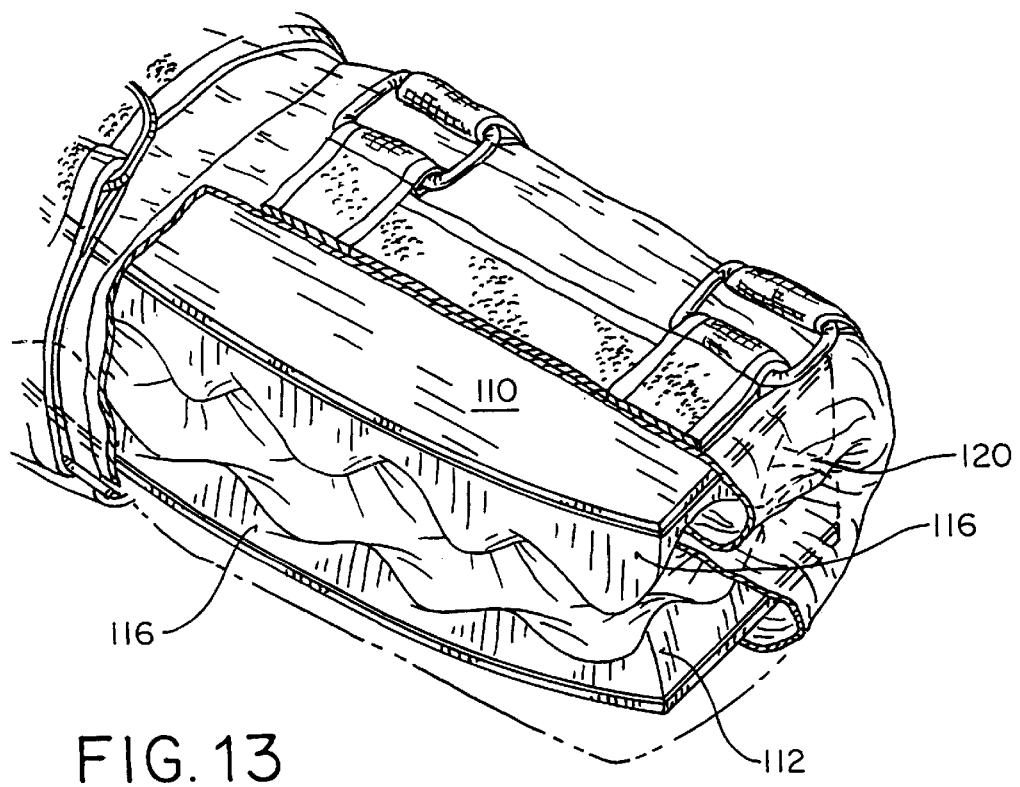
FIG. 13 is a detailed view, similar to FIG. 12, shown in partial section.

An alternative construction of the sleeve of the present invention is illustrated in FIGS. 11–13. The sleeve 100 is generally similar to the sleeve illustrated in FIG. 1, except that an outer sleeve 102 comprises an axial fastener in the form of a zipper 104 which permits the entire length of the sleeve to be opened and closed to facilitate inserting and withdrawing the arm A from the sleeve. In some cases, it may be sufficient to employ only the zipper 104 to apply a preselected level of pressure onto the arm. Usually, however, it will still be desirable to provide a plurality of separate straps 106 which may be constructed as generally described above.

A further difference in the sleeve 100 is the inclusion of a pair of opposed plates 110 and 112, as best observed in FIGS. 12 and 13. The plates 110 and 112 help apply pressure to the convoluted foam which engage the hand to the inner sleeve material 120.

In using the devices of FIGS. 1 and 11, it is important to apply pressure at the spaced-apart locations on the body surface in a uniform manner. The pressure applied should be relatively high, but should always be maintained below venous pressure in order to permit continued blood flow and allow lymphatic and other fluid drainage. The applied pressure may be measured by interposing a fluid-filled bladder between the body surface and the inner radial tips of the pressure-applying fingers. The outer sleeve of the device can then be tightened sufficiently so that the pressure applied by the fingers to the bladder is in the range from 5 mmHg to 60 mmHg, preferably from 10 mmHg to 45 mmHg. The pressure should be applied for a time sufficient to reduce swelling, typically being employed overnight. Often, initial treatment will involve daily (or nightly) treatments, with maintenance treatments occurring once or twice a week.

The devices illustrated in FIGS. 1 and 11 have been successfully employed in a number of test cases. In one case, an arm which had been swollen of excess lymphatic fluids was reduced in circumference by 50 mm (2") in 2 hours, whereas other prior art pressure devices which had been used over several days had produced no appreciable reduction. Similar results were obtained with other patients. Another patient who had been using prior art pressure devices without success and who also had suffered frequent infections to her arm, was fitted with the present invention on a 12 month trial basis; the swelling was soon reduced and no further infections.

Although the present invention is especially directed toward the treatment of lymphedema, it is envisioned as also being applicable for prevention and/or treatment of embolism or thrombosis, as well as for treatment of swollen limbs resulting from venous insufficiency.

Those skilled in the art will envision that many other possible variations are within its scope. For example skilled artisans will readily be able to change the thickness or density of the foam, or length of convolutes, or assembly different combinations of foam, or design a different configuration of pressure points and channels. It is possible to change the arrangement, or widths of the VELCRO bands or use different grades of VELCRO. It is possible to fit other forms of loops, or means to grasp the VELCRO bands when making adjustments. Any suitable material can be sued to cover the elastomeric pressure material, including fabric printed with patterns. Other types of foam material such as rubber, plastic air bubbles, foam air bubbles or non-convolute foam and the like can be used. Different means of installation can be used. Various heights of convolutes can be used to conform to limb shape, and various number of convolutes per square foot can be used.

Accordingly, the reader is requested to determine the scope of the invention by the appended claims and their legal equivalents, and not by the examples which have been given.

What is claimed is:

1. An apparatus for applying pressure to a body part of a patient, said apparatus comprising:
    an outer sleeve configured to encircle and extend the entire length of said body part;
    a multiplicity of pressure-applying resilient protrusions within the outer sleeve, the protrusions being configured to encircle and extend over the entire surface of the body part and to apply pressure to a surface of said body part of said patient; and
    strap means spaced along said outer sleeve for radially compressing the resilient protrusions onto the body part.

2. The apparatus of claim 1 wherein said multiplicity of pressure applying protrusions are spaced apart to provide a multiplicity of high pressure points or lines within said body part.

3. The apparatus of claim 1 wherein the fingers have a height from a base to a tip in the range from 0.5 cm to 15 cm.

4. The apparatus of claim 3 wherein the protrusions comprise fingers arranged in a generally cylindrical envelope with individual fingers being aligned radially with respect to the axis of the cylindrical envelope.

5. The apparatus of claim 4 intended for applying pressure to an arm wherein the length of the cylinder is in the range from 3 cm to 200 cm, the bases of the fingers are distributed over a generally cylindrical surface having a diameter in the range from 7.5 cm to 75 cm, and the tips of the fingers are distributed over a generally cylindrical surface having a diameter in the range from 2 cm to 25 cm.

6. The apparatus of claim 4 wherein the outer sleeve secures the bases of the finger over a generally cylindrical surface.

7. The apparatus of claim 6 wherein the outer sleeve is formed form a non-distensible fabric which can be rolled to form the cylindrical surface.

8. The apparatus of claim 7 further comprising an axial fastener which allows the rolled fabric to be opened and closed.

9. The apparatus of claim 1 wherein the structure for radially compressing the resilient protrusions comprises a plurality of straps which allow the rolled fabric to be adjustably radially inwardly compressed.

10. The apparatus of claim 4 further comprising an inner sleeve which covers the tips of the fingers over a generally cylindrical surface.

11. The apparatus of claim 1 wherein said multiplicity of protuberances comprises a sheet of convoluted plastic foam.

12. The apparatus of claim 1 wherein said multiplicity of pressure applying fingers are configured to apply pressure in a pattern encircling a limb of a patient to provide a multiplicity of high pressure points or lines within said limb of said patient.

13. The apparatus of claim 1 wherein said outer sleeve is configured to encircle an arm of said patient.

14. The apparatus of claim 1 wherein said outer sleeve is configured to encircle a leg of said patient.

15. The apparatus of claim 1 wherein said outer sleeve is configured to encircle a torso of said patient.

16. The apparatus of claim 1 further comprising an inner sleeve interposed between said multiplicity of pressure applying fingers and said limb of said patient.

17. The apparatus of claim 5 further comprising a pair of opposed plates arranged to engage opposite sides of a patient's hand when the cylindrical envelope is disposed over an arm.

18. An apparatus for treating lymphedema in a limb of a patient comprising:

an outer sleeve configured to encircle and extend along the entire length of said limb of said patient, a sheet of convoluted plastic foam within said outer sleeve having a multiplicity of protuberances defining a multiplicity of inwardly directed pressure applying fingers configured to apply pressure in a grid-like pattern to a surface of said limb of said patient, said pressure applying fingers being spaced apart to provide a multiplicity of high pressure points within said limb of said patient and a multiplicity of lower pressure channels between said multiplicity of high pressure points, an inner sleeve interposed between said multiplicity of pressure applying fingers and said limb of said patient, and a plurality of strap means configured to tighten said outer sleeve about said pressure applying fingers upon said limb of said patient.

19. The apparatus of claim 18 wherein said outer sleeve is configured to encircle an arm of said patient.

20. The apparatus of claim 18 wherein said outer sleeve is configured to encircle a leg of said patient.

* * * * *